US006858234B2

(12) United States Patent
Murayama et al.

(10) Patent No.: US 6,858,234 B2
(45) Date of Patent: Feb. 22, 2005

(54) PROCESS FOR THE PREPARATION OF AMYLASE INHIBITOR

(75) Inventors: Ryuji Murayama, Hyogo (JP); Takeo Kanafuji, Hyogo (JP); Yasuhito Muranaka, Hyogo (JP); Rumiko Muranaka, Hyogo (JP); Kazuo Sato, Ueda (JP); Akira Sekigawa, Ueda (JP); Kazuhiko Yamada, Saitama (JP); Yoshio Suzuki, Saitama (JP); Hiroyuki Ikemoto, Saitama (JP)

(73) Assignees: Nisshin Pharma Inc. (JP); Nagata Sangyo Co., Ltd. (JP)

(*) Notice: Subject to any disclaimer, the term of this patent is extended or adjusted under 35 U.S.C. 154(b) by 0 days.

(21) Appl. No.: 10/349,714

(22) Filed: Jan. 23, 2003

(65) Prior Publication Data

US 2003/0186409 A1 Oct. 2, 2003

(30) Foreign Application Priority Data

Jan. 25, 2002 (JP) .......................... 2002-016573
Jan. 25, 2002 (JP) .......................... 2002-016574

(51) Int. Cl.$^7$ .................. A61K 35/78; A61K 38/00; C12N 9/26
(52) U.S. Cl. .................. 424/750; 435/183; 435/291; 514/2
(58) Field of Search .................. 424/750; 435/183, 435/201; 514/2

(56) References Cited

U.S. PATENT DOCUMENTS

| 3,950,319 | A | * | 4/1976 | Schmidt et al. .............. 530/374 |
| 5,084,275 | A | * | 1/1992 | Maeda et al. ................ 424/750 |
| 5,332,803 | A | | 7/1994 | Miyazaki et al. |
| 5,444,046 | A | * | 8/1995 | Miyazaki et al. .............. 514/12 |
| 5,726,291 | A | * | 3/1998 | Miyazaki et al. ............ 530/375 |

FOREIGN PATENT DOCUMENTS

| EP | 0039962 | * | 11/1981 |
| EP | 0 039 962 A1 | | 11/1981 |
| EP | 0372522 | * | 6/1990 |
| EP | 0 567 088 A2 | | 4/1993 |
| GB | 1 330 230 A | | 9/1973 |
| JP | 46-1833 A1 | | 10/1971 |
| JP | 61-171431 A1 | | 2/1986 |
| JP | 04-182500 A | | 6/1992 |
| JP | 04182500 | * | 6/1992 |
| JP | 07-048268 A1 | | 1/1995 |
| JP | 07048268 | * | 2/1995 |
| JP | 09094065 | * | 4/1997 |
| JP | 09172999 | * | 7/1997 |

OTHER PUBLICATIONS

Granum, P.E. et al., "Purification and Characterization of α–Amylase Inhibitors in Wheat (*Triticum Aestivum* Var. Anza)", *Journal of Food Biochemistry*, 1977, pp. 385–401, pub. 1978 Dep. of Microbiol., Norwegian Food Res. Inst., 1432 AS–NLH, Norway, vol. 1, No. 4, XP009010649.

Silano, V. et al., "Varietal Differences in Albumin and Globulin Fractions of *Triticum Aestivum* and *T. Durum*", *J. Sci. Fd Agric.*, 1969, pp. 260–262, vol. 20, May.

\* cited by examiner

*Primary Examiner*—Christopher R. Tate
(74) *Attorney, Agent, or Firm*—Webb Ziesenheim Logsdon Orkin & Hanson, P.C.

(57) ABSTRACT

The process for the preparation of amylase inhibitor including the steps of: (A) obtaining an extract solution containing the amylase inhibitor; (B) insolubilizing the amylase inhibitor by salting out by addition of a salt or salts to the solution obtained in the step (A) and recovering the insolubilized substance resulting from the salting out; and (C) directly drying the insolubilized substance recovered in the step (B) or dissolving the insolubilized substance in water to prepare an aqueous solution, and desalting and drying the aqueous solution to recover the amylase inhibitor, whereby, an amylase inhibitor in high concentrations 0.19 AI is prepared that shows highly inhibitive activity against the amylase in high yield and with good productivity.

13 Claims, No Drawings

PROCESS FOR THE PREPARATION OF AMYLASE INHIBITOR

FIELD OF THE INVENTION

The present invention relates to a process for the preparation of amylase inhibitor from wheat flour or wheat gluten, which is simple but productive to realize high yields.

BACKGROUND OF THE INVENTION

Patients suffering metabolic diseases, such as diabetes, are rapidly increasing due to the recent rich and varied diet. Intake of excessive nutrients induces oversecretion of insulin to cause indirectly a metabolic unbalance, thus leading to glucose intolerance (hyperglycemia), diabetes, hyperlipemia, arteriosclerosis, etc. Diabetic patients in particular suffer insufficient insulin function and glucose intolerance so that their blood glucose level drastically increases after meals to invite complications such as damages in blood capillaries and arteriosclerosis.

It is thought effective for prevention and treatment of such diseases to take in medications or foods that will depress the rise of blood glucose level after intake of essential nutrients or that will inhibit excessive secretion of insulin. Therefore a substance capable of controlling or inhibiting the hydrolysis of ingested starch into glucose and a substance capable of controlling the insulin secretion are demanded.

From the above aspects, various studies have been made on amylase inhibitors that inhibit an activity of an amylase from hydrolyzing starch into glucose. Since the report that wheat contains the amylase inhibitor, the research and development of the amylase inhibitors of wheat origin have been carried out.

The wheat-origin amylase inhibitors include 0.19 AI (AI: amylase inhibitor), a protein constructed of two subunits each consisting of 124 amino acid residues and having the molecular weight 13,337, in which a single band is observed at the mobility 0.19 by polyacrylamide gel electrophoresis (Swiss Port: ID=IAA1_WHEAT); 0.28 AI, a protein constructed of two subunits each consisting of 123 amino acid residues and having the molecular weight 13,326, in which a single band is observed at the mobility 0.28 by polyacrylamide gel electrophoresis (U.S. Pat. No. 5,444,046, Swiss Port: ID=IAA2_WHEAT); and a protein constructed of two subunits each consisting of 124 amino acid residues and having the molecular weight 13,185, in which a single band is observed at the mobility 0.53 by polyacrylamide gel electrophoresis (U.S. Pat. No. 5,726,291, Swiss Port: ID=IAA5_WHEAT). These amylase inhibitors are known to be effective in inhibiting the rise in the blood glucose level and controlling the insulin secretion. The mobility according to the polyacrylamide gel electrophoresis is based on the mobility 1 of bromphenol phenol according to the polyacrylamide gel electrophoresis (7.5%, pH 9.5), as described in J Sci. Food Agric., 20, pp. 260–261 (1969).

JP-A-46(1971)/1833 and JP-A-61(1986)/171431 disclose that the amylase inhibitors extracted from wheat with water, an acid or an aqueous alcohol may be used in treatments of diabetes and obesity. However, these conventional amylase inhibitors of wheat origin do not produce as much results as expected when orally administered to humans; they can achieve only a limited effect of inhibiting the digestion (hydrolysis) of heat cooked starch, such as of cooked rice, into glucose and are expensive.

U.S. Pat. No. 5,332,803 discloses a process for the preparation of amylase inhibitor, which comprises the steps of extracting wheat, wheat flour or wheat gluten with water, an acidic aqueous solution, an alkali aqueous solution or an aqueous alcohol to produce an extract solution (the solution may be otherwise a starch wastewater discharged in the process of recovery of starch from wheat flour, etc.); adding a polysaccharide, such as sodium alginate, to the extract solution to form an insoluble complex; recovering the complex from the solution and dissolving or dispersing it in a solvent; dissociating the polysaccharide from the complex and removing it from the solution; treating the resultant solution with a cation exchange resin; and recovering the amylase inhibitor from the fractions passed through the cation exchange resin. The amylase inhibitor produced by the above process shows a very high inhibitory activity against the amylase but hardly against trypsin. The amylase inhibitor also has a high inhibitory activity against the amylase contained in pancreatic juice so that it is very effective in controlling the insulin secretion.

The method of JP-A-7 (1995)/48268 is capable of treating a large amount of materials with good operability while reducing wastes so that the mass production of the objective amylase inhibitor can be obtained. The method, which also uses the above amylase inhibitor-containing solution (of the U.S. Pat. No. 5,332,803) obtained by removing from the liquid the polysaccharide dissociated from the insoluble complex of the amylase inhibitor and the polysaccharide, comprises the steps of precipitating 40–70% of the protein contained in the solution; dissolving the precipitated protein in water to prepare another solution containing the amylase inhibitor; adding calcium and phosphoric ions to the newly obtained solution to insolubilize a complex containing the amylase inhibitor and recovering it from the solution; and solubilizing the amylase inhibitor of the insolubilized complex in water to obtain a solution containing the amylase inhibitor. The resulting final product contains the amylase inhibitor in high concentration and has a stronger amylase inhibitory activity.

According to the methods disclosed in U.S. Pat. No. 5,332,803 and JP-A-7(1995)/48268, the obtainable amylase inhibitors contain in high concentrations 0.19 AI that has a very high inhibitory activity against the amylase but not against or hardly against trypsin. The amylase inhibitors obtained by these methods are highly inhibitive against the amylase contained in pancreatic juice and are therefore effective in controlling the insulin secretion. Accordingly those amylase inhibitors can be an effective suppressant for the hydrolysis of heat cooked starch, such as of cooked rice, into glucose.

However, the method of U.S. Pat. No. 5,332,803 involves the use of cation exchange resin, which necessitates washing of the cation exchange resin after preparation of the amylase inhibitor so that it can be reused. The process of JP-A-7 (1995)/48268 comprises so many steps that it is complicated. Thus, the advent of a simpler and more efficient process capable of quick production of the amylase inhibitor with good productivity is demanded.

It is accordingly an object of the present invention to provide a process for the preparation of amylase inhibitor, the process being simple and productive so that the amylase inhibitor containing in high concentrations 0.19 AI that is highly inhibitive against the amylase can be obtained quickly and in high yields.

SUMMARY OF THE INVENTION

The process for the preparation of amylase inhibitor according to the present invention comprises:

(A) a step of obtaining an extract solution containing the amylase inhibitor by:

(A1) extracting wheat flour or wheat gluten with water, an acidic aqueous solution, an alkali aqueous solution or an aqueous alcohol, (A2) extracting wheat flour or wheat gluten with water, an acidic aqueous solution, an alkali aqueous solution or an aqueous alcohol; acid-treating and/or heat-treating the resulting solution to denature the contaminants; and removing the denatured contaminants from the solution, or (A3) adding a polysaccharide to the amylase inhibitor-containing solution obtained in (A1) or (A2) to form an insoluble complex of the amylase inhibitor and the polysaccharide; and dissociating the polysaccharide from the insoluble complex to remove the polysaccharide in an insolubilized form from the solution;

(B) a step of insolubilizing the amylase inhibitor by salting out by addition of a salt or salts to the amylase inhibitor-containing solution obtained in the step (A) and recovering the insolubilized substance resulting from the salting out; and (C) a step of directly drying the insolubilized substance recovered in the step (B) or dissolving the insolubilized substance in water to prepare an aqueous solution, and desalting and drying the aqueous solution to recover the amylase inhibitor.

In the above process, the salt in the step (B) is preferably sodium chloride. The salting out is preferably carried out in the presence of calcium ions in the extract solution. Also preferably, the salting out is carried out in the extract solution adjusted the pH within the range of 3 to 4.

In the above process, at least one of the steps (B) and (C) preferably includes addition of ascorbic acid and/or cysteine.

Preferably, the solution containing the amylase inhibitor for use in the salting out in the step (B) is a concentrate of the solution obtained in the step (A). The concentrate preferably has a protein concentration of 1 to 100 mg/cm$^3$.

The process for the concentration of extract solution containing the amylase inhibitor according to the present invention comprises the steps of:

(I) adjusting the pH of an extract solution containing the amylase inhibitor within the range of 4.5 to 5.5, adding a polysaccharide to the solution to form an association product of the amylase inhibitor and the polysaccharide in the solution and then adjusting the pH within the range of 3.0 to 4.0 to form an insoluble complex of the amylase inhibitor and the polysaccharide; and (II) separating the insoluble complex from the solution, dissociating the polysaccharide from the insoluble complex, and removing the polysaccharide in an insolubilized form from the solution to recover the amylase inhibitor in the form of solution.

In the above concentration process, the polysaccharide is preferably dissociated from the insoluble complex of the amylase inhibitor and the polysaccharide under the influence of glucanase, and the dissociated polysaccharide is preferably removed in an insolubilized form by filtration. The filtration is preferably carried out with addition of a filter aid. Preferably, the solution containing the amylase inhibitor is heated at 50° C. or above during or after the dissociation of the polysaccharide.

The present patent application is claiming priority based on Japanese Patent Application Nos. 2002-16573 and 2002-16574, which will be incorporated herein by reference.

DETAILED DESCRIPTION OF THE INVENTION

The process for the preparation of amylase inhibitor according to the invention is described below.

Step (A)

In the step (A), the extract solution containing the amylase inhibitor is prepared from wheat flour or wheat gluten. The extract solution containing the amylase inhibitor is preferably obtained by either the step (A1), (A2) or the step (A3):

(A1) the step of extracting wheat flour or wheat gluten with water, an acidic aqueous solution, an alkali aqueous solution or an aqueous alcohol;

(A2) the step of extracting wheat flour or wheat gluten with water, an acidic aqueous solution, an alkali aqueous solution or an aqueous alcohol; acid-treating and/or heat-treating the resulting solution to denature the contaminants; and removing the denatured contaminants from the solution;

(A3) adding a polysaccharide to the amylase inhibitor-containing extract solution obtained in (A1) or (A2) to form an insoluble complex of the amylase inhibitor and the polysaccharide; and dissociating the polysaccharide from the insoluble complex to remove the polysaccharide in an insolubilized form from the solution.

The extraction in the step (A1) or (A2) may be conducted with the use of any of water, an acidic aqueous solution, an alkali aqueous solution and an aqueous alcohol.

When the extraction in the step (A1) or (A2) is conducted using water, the extraction conditions are not particularly limited and the extract solution may be obtained from wheat flour or wheat gluten by any appropriate method.

For example, starch or gluten is generally obtained from wheat flour as follows: wheat flour and water are kneaded together to form a dough or batter, which is then aged to thoroughly hydrate the gluten, and the dough is repeatedly washed with water to give gluten and starch milk (gluten wash liquid), and the starch milk is subjected to a separation such as mechanical separation, thereby recovering the starch. The solution discharged as above contains the amylase inhibitor so that it can be used as the extract solution in the present invention. This is extremely advantageous since the liquid usable as the extract solution is a waste liquid discharged in production of starch and gluten by Martin's or Batter's method.

When the extraction in the step (A1) or (A2) is conducted using an acidic aqueous solution, the acidic aqueous solution is desirably prepared by adding water to an inorganic acid, such as hydrochloric acid, phosphoric acid, etc., or an organic acid, such as acetic acid, etc., such that the resulting acidic aqueous solution is adjusted to the pH within the range of about 2 to 6, preferably 2 to 4.

When the extraction in the step (A1) or (A2) is conducted using an alkali aqueous solution, the alkali aqueous solution is desirably prepared by adding ammonia or sodium hydroxide or the like to water such that the resulting alkaline aqueous solution is adjusted to the pH about 8 to 10.

When the extraction in the step (A1) or (A2) is conducted using an aqueous alcohol, it is ideal to use an alcoholic aqueous solution of about 1 to 50% alcohol concentration. Examples of the alcohol used herein include methanol, ethanol and isopropyl alcohol.

The extraction in the step (A1) or (A2) is ordinary carried out with stirring at temperatures of about 10 to 40° C., for example at room temperature.

In the step (A1), the solid matters in the liquid are removed by such an appropriate means as centrifugal separation, filtration or standing, thereby obtaining the extract solution containing the amylase inhibitor.

In the step (A2), the extract solution is subjected to acid treatment and/or heat treatment to denature the contaminating proteins and those proteins are removed from the solution so that the extract solution containing the amylase inhibitor may be obtained. The acid treatment is preferably carried out by allowing the extract solution containing the amylase inhibitor to stand at the pH 2 to 4, and the heat treatment is preferably carried out by heating the solution at temperatures from 70 to 90° C., more preferably from 85 to 90° C. Those treatments are capable of denaturing the contaminating proteins, contained in the amylase inhibitor-containing extract solution, to render them insoluble in water so that the water-insolubilized contaminating proteins can be removed from the solution by such an appropriate means as centrifugal separation, filtration or standing. The thus-obtained extract solution containing the amylase inhibitor is then subjected to the step (B).

In the step (A3), a polysaccharide capable of forming an insoluble complex together with the amylase inhibitor is added to the amylase inhibitor-containing extract solution obtained in the step (A1) or (A2) to form such an insoluble complex. The insoluble complex thus formed is separated from the solution thus a dissociation liquid is added to the separated insoluble complex. The polysaccharide is then dissociated from the insoluble complex and removed in an insolubilized form from the dissociation liquid. Thus, the amylase inhibitor can be obtained in the form of solution. The extract solution obtained in the step (A3) has been concentrated so that it contains the amylase inhibitor in higher concentrations.

The polysaccharide for use in the step (A3) may be any one capable of forming the insoluble complex together with the amylase inhibitor. Examples include polysaccharides capable of cation exchange, such as sodium alginate, carboxymethyl cellulose, K-carrageenan, v-carrageenan and λ-carrageenan; pectin, xanthan gum and gellan gum. Of these, sodium alginate is preferable from the viewpoint of yield of the insoluble complex.

The polysaccharide is added usually in an amount of 50 to 600 ppm to the extract solution containing the amylase inhibitor obtained in the step (A1) or (A2).

In the step (A3), the association product of the amylase inhibitor and the polysaccharide is formed by adjusting the pH of the extract solution within the range of 2 to 5.5, preferably 4.5 to 5.5, and adding a polysaccharide to the solution. The pH of the solution is then adjusted to 3.0 to 4.0 to induce formation of the insoluble complex of the amylase inhibitor and the polysaccharide. The insoluble complex thus formed is so a large agglomerate that it can be readily recovered by an appropriate means such as filtration.

In the step (A3), the formation of the insoluble complex of the amylase inhibitor and the polysaccharide may take place on heating, but preferably at room temperature or with cooling. The resulting insoluble complex may be separated from the solution by such an appropriate means as gravity setting, filtration, centrifugal separation, etc.

The polysaccharide is dissociated from the insoluble complex of the amylase inhibitor and the polysaccharide in a dissociation liquid and then removed in an insolubilized form from the liquid. Thus, the amylase inhibitor is recovered in the form of solution.

Step (B)

In the step (B), the amylase inhibitor is insolubilized by salting it out by addition of a salt or salts to the solution obtained in the step (A) and the insolubilized substance resulting from the salting out is recovered.

The extract solution obtained in the step (A1) or (A2) may be directly subjected to the step (B) or maybe concentrated by the method of the step (A3) or other conventional concentration method.

The use of the concentrated solution is preferable since the amylase inhibitor has higher concentration in the solution so that it can be salted out in high yield by addition of a salt or salts, thereby realizing higher yield of the amylase inhibitor. The degree of concentration, which is appropriately adjusted depending on the amylase inhibitor content in the extract solution to be concentrated, is usually such that the protein concentration in the concentrated solution falls within 1 to 100 mg/cm$^3$. This concentration is preferable from the viewpoints of yield of the amylase inhibitor, control of the contamination of the solution by impurities, operability, etc.

The extract solution containing the amylase inhibitor may be concentrated by the method of the step (A3), vacuum concentration, ultrafiltration or the like.

When the extract solution contains any proteins other than the amylase inhibitor that are dispersed or precipitated therein as insoluble impurities, those impurities are preferably removed from the solution by filtration, centrifugal separation, decantation, etc., before the extract solution is subjected to the salting out in the step (B).

Since the concentrated extract solution often contains dispersed impurities such as proteins besides the amylase inhibitor, the salting out is ideally carried out after those impurities are removed by acid treatment or alginic acid treatment or the like.

Examples of the salt for use in the salting out of the amylase inhibitor in the step (B) include sodium chloride, potassium chloride, ammonium sulfate, sodium sulfate, potassium sulfate and calcium phosphate, with sodium chloride and ammonium sulfate being preferred. Above all, sodium chloride is particularly preferable since it is capable of satisfactorily separating the amylase inhibitor from the solution obtained in the step (A) and it can be readily removed in the following step (C). Also, sodium chloride causes little environmental pollution.

The amount of salt used for the salting out may be adjusted depending on the type of the salt, the concentration of the amylase inhibitor in the extract solution, whether the extract solution has been concentrated, and the degree of concentration. The salt is generally used in an amount such that its concentration in the solution falls within 1 to 20 wt %, especially about 3 to 15 wt %, this concentration being preferable since it allows favorable separation of the amylase inhibitor while preventing other proteins from being salted out.

The salt, such as sodium chloride or ammonium sulfate, may be used for the salting out individually or in combination with a compound that generates calcium ions (calcium chloride, calcium bromide, calcium carbonate, etc.). The salting out in the presence of calcium ions allows for separation of the amylase inhibitor in higher yields. The concentration of calcium ions in the solution is preferably about 100 to 10,000 ppm in view of accelerated effect for the salting out.

The temperature of the solution during the salting out in the step (B) is preferably 50° C. or below, particularly 30° C. or below since the amylase inhibitor can be smoothly salted out at the temperatures. The salting out at liquid temperatures over 50° C. may result in denaturation or deactivation of the amylase inhibitor.

The pH of the solution at the salting out is preferably within 2 to 8, more preferably 3 to 4 from the viewpoint of efficient salting out of the amylase inhibitor. The salting out at the pH of the liquid less than 2 or exceeding 8 results in decreased efficiency of the salting out, lowering the yield of the amylase inhibitor.

The insolubilized substance (salted out product) resulting from the salting out that contains the amylase inhibitor is separated and recovered from the solution. The method for separating and recovering the salted out product is not particularly limited and can be decantation, filtration, centrifugal separation or gravity setting. The salted out product obtained in the step (B) can be readily separated from the liquid phase so that the separation and recovery thereof can be smoothly achieved by a general solid-liquid separation method.

The salted out product obtained in the step (B) is then subjected to the step (C).

Step (C)

The step (C) is either (i) a step of directly drying the insolubilized substance recovered in the step (B.) or (ii) a step of dissolving the insolubilized substance in water to prepare an aqueous solution, and desalting and drying the solution to recover the amylase inhibitor.

In the case of the step (ii), the insolubilized substance (salted out product) containing the amylase inhibitor is preferably dissolved in water which temperature of 10 to 85° C., particularly 20 to 40° C. since the water temperature accelerates dissolution of the salted out product in water and causes no denaturation of the amylase inhibitor.

The water is preferably used in a mass 3 to 30 times that of the salted out product.

In the step (ii), the salt may be removed from the aqueous solution of the salted out product by means of ultrafiltration, dialysis, ion exchange, etc. Of these, the ultrafiltration is preferable because of easy maintenance of the equipment.

In the step (ii), a treatment (such as filtration) to remove impurities and bacteria may be optionally carried out before, during or after the removal of the salt from the aqueous solution of the salted out product. The removal of impurities and bacteria may be achieved by means of a microfiltration membrane, a porous polymer membrane, a ceramic filter, etc.

The drying treatment in the step (C) to recover the amylase inhibitor may be freeze drying, vacuum drying, spray drying or ball drying. Of these, freeze drying or vacuum drying is preferable from the viewpoint of prevention of denaturation of the amylase inhibitor. The aqueous solution containing the amylase inhibitor may be subjected to the drying treatment directly or after it is concentrated. The latter case is preferable in terms of drying efficiency and bulk specific gravity of the final product.

At least one of the steps (B) and (C) preferably contains addition of ascorbic acid and/or cysteine. The addition leads to inhibition of coloring of the solution so that the resulting amylase inhibitor will be excellent in color, taking on a white or like tone.

The amount of ascorbic acid and/or cysteine used is preferably 1 to 1,000 $g/m^3$ based on the liquid amount. The reason as to why the ascorbic acid and cysteine have capability of inhibiting the coloring of the amylase inhibitor-containing solution is presumably that they are able to neutralize or decrease the activity of enzyme contained in the solution that is partially responsible for the coloring of the liquid.

By the above process for the preparation of amylase inhibitor comprising the steps (A) to (C), the amylase inhibitor containing in high concentrations 0.19 AI, which is highly inhibitive against the amylase, can be obtained quite readily, quickly, in large amounts and with good productivity.

Next, the process for the concentration of extract solution containing the amylase inhibitor will be described.

The concentration process comprises the steps of:

(I) adjusting the pH of an extract solution containing the amylase inhibitor within the range of 4.5 to 5.5, adding a polysaccharide to the solution to form an association product of the amylase inhibitor and the polysaccharide in the solution and then adjusting the pH within the range of 3.0 to 4.0 to form an insoluble complex of the amylase inhibitor and the polysaccharide; and (II) separating the insoluble complex from the solution, dissociating the polysaccharide from the insoluble complex, and removing the polysaccharide in an insolubilized form from the liquid to recover the amylase inhibitor in the form of solution.

Step (I)

Although it is not particularly limited thereto, the extract solution containing the amylase inhibitor for use in the concentration process is preferably obtained by either the step (A1) or the step (A2) of the present process for the preparation of amylase inhibitor.

The polysaccharide for use in the step (I) may be any one capable of forming the insoluble complex together with the amylase inhibitor. Examples include polysaccharides capable of cation exchange, such as sodium alginate, carboxymethyl cellulose, κ-carrageenan, ν-carrageenan and λ-carrageenan; pectin, xanthan gum, gellan gum and the like. Sodium alginate is preferable from the viewpoint of yield of the insoluble complex.

The polysaccharide is added usually in an amount of 50 to 600 ppm to the extract solution containing the amylase inhibitor.

In the step (I), the extract solution containing the amylase inhibitor is first adjusted to the pH 4.5 to 5.5, then the polysaccharide is added to the solution to form the association product, and the pH of the mixture solution is adjusted within the range of 3.0 to 4.0.

By previously adjusting the pH of the extract solution within the range of 4.5 to 5.5, the association product of the amylase inhibitor and the polysaccharide can be formed at a high efficiency once the polysaccharide is added to the solution. By the subsequent adjustment of the pH within 3.0 to 4.0, the insoluble complex will be formed so a large agglomerate that it can be readily recovered from the solution by gravity setting or centrifugal separation. As a result, the amylase inhibitor can be recovered from the extract solution in high yields. The recovery percentage for the amylase inhibitor from the extract solution is generally not less than 80 wt %.

When the polysaccharide is added to the extract solution whose pH is less than 4.5 or exceeds 5.5, the association of the amylase inhibitor and the polysaccharide cannot be thoroughly achieved so that the recovery of the amylase inhibitor will be lowered.

The pH adjustment of the extract solution may be carried out by use of an acid, such as hydrochloric acid or phosphoric acid, or an alkali, such as sodium hydroxide or potassium hydroxide, which can be appropriately selected depending on the pH of the extract solution.

In the step (I), the formation of the insoluble complex of the amylase inhibitor and the polysaccharide may take place on heating, but preferably at room temperature or with cooling within the range of 1 to 30° C.

In general, the insoluble complex is formed at temperatures about 1 to 30° C. in the following manner: the polysaccharide is added to the extract solution previously adjusted to the pH 4.5 to 5.5, the mixture solution is continuously stirred for several tens of minutes to several hours, the pH is then adjusted to 3.0 to 4.0 and the mixture solution is continuously stirred for several tens of minutes to several hours. The insoluble complex thus formed is so a large agglomerate that it can be readily recovered from the solution in the step (II) by an appropriate means such as gravity setting, filtration, centrifugal separation, etc. According to the step (I), the insoluble complex of the amylase inhibitor and the polysaccharide forms a large agglomerate to allow for easy separation.

Step (II)

In this step, the insoluble complex of the amylase inhibitor and the polysaccharide obtained in the step (I) is separated from the solution, a dissociation liquid is added to the separated insoluble complex, and the polysaccharide in an insolubilized form (insolubilized polysaccharide) is removed from the liquid to obtain the amylase inhibitor in the form of solution.

In the step (II), the insoluble complex can be recovered by an appropriate means such as gravity setting, filtration, centrifugal separation, etc.

In the step (II), the separation of the polysaccharide from the insoluble complex is performed in a dissociation liquid by adding a dissociation liquid to the recovered insoluble complex. In the dissociation liquid, the amylase inhibitor and the polysaccharide that have formed the insoluble complex are dissociated from one another and are dissolved or swollen in the dissociation liquid. The dissociation liquid used herein may be water, a weak-alkaline aqueous solution containing ammonia, ammonium hydrogen carbonate carbonate, etc., or an aqueous solution of a salt containing neither calcium nor potassium.

Although the dissociation of the insoluble complex into the amylase inhibitor and the polysaccharide can take place at room temperature, the dissociation liquid is preferably heated at 30° C. or above to accelerate the dissociation.

In particular, the solution containing the amylase inhibitor is preferably heated at 50° C. or above, more preferably 60° C. or above, particularly 80° C. or above at least once during or after the dissociation of the insoluble complex, since the resulting liquid will be colorless or a like color (light yellow) instead of the usual brown so that the final product of the amylase inhibitor in dry powder will take on a white or like tone.

When metal ions, such as of calcium or magnesium, are added to the solution in which the amylase inhibitor and the polysaccharide are dissociated from each other, the polysaccharide is insolubilized to form a solid gel while the amylase inhibitor stays dissolved in the liquid. The resulting solution is then subjected to an appropriate separation method to remove the gel of insolubilized polysaccharide. Thus, the solution containing the amylase inhibitor can be recovered.

Sodium alginate, K-carrageenan, ν-carrageenan and λ-carrageenan are readily insolubilized to form a solid gel on addition of the metal ions, such as of calcium or magnesium. For example, when calcium chloride is added to the solution that contains dissociated sodium alginate, the gel of calcium alginate is readily formed.

The insolubilized polysaccharide may be separated or removed by means of filtration, centrifugal separation or other separation methods, with the filtration being preferable in terms of yield and purity for the amylase inhibitor.

When the insolubilized polysaccharide, resulting from the dissociation of the insoluble complex, is removed by filtration, the filtration will suffer clogging due to the poor filterability of insolubilized polysaccharide, taking long time for completion.

Therefore, the solid polysaccharide (insolubilized polysaccharide) can be removed under the influence of glucanase, which is added to the solution when the insoluble complex is dissociated into the amylase inhibitor and the polysaccharide and/or when the dissociated polysaccharide is insolubilized (gelled). The addition of glucanase enhances the filterability of insolubilized polysaccharide so that the insolubilized polysaccharide can be efficiently removed by filtration.

The term glucanase means the all enzymes capable of hydrolyzing glucose polysaccharide (glucan) into oligosaccharide or glucose. The glucanase for use in the invention may be any enzyme, for example Cellulosin (available from HANKYU KYOEI BUSSAN).

The glucanase may be added to the solution prior to the dissociation of polysaccharide from the insoluble complex, during the dissociation of the insoluble complex into the amylase inhibitor and the polysaccharide, or at the insolubilization (gelatinization) of the dissociated polysaccharide. The glucanase is preferably added during the dissociation of the insoluble complex in view of enhanced filterability of the resulting polysaccharide gel (insolubilized polysaccharide).

The glucanase is added preferably in an amount of at least 0.1 mg, more preferably from 1 to 100 mg based on 1 liter of the solution or suspension containing either the insoluble complex or the dissociated amylase inhibitor and polysaccharide.

The filterability of the insolubilized polysaccharide may be further enhanced by addition of a filter aid together with the glucanase so that the insolubilized polysaccharide dissociated from the insoluble complex may be removed by filtration even more smoothly. Examples of the filter aid include the Radiolite series produced by Showa Chemical Industry Co., Ltd., the Celite series produced by Celite Corporation, talk and the like, which may be used either individually or in combination.

The filter aid is used preferably in a fortieth mass or more, still preferably a thirtieth mass or more of the solid matters to be filtered out (mainly the insolubilized polysaccharide).

The filter aid may be added to the solution prior to the dissociation of polysaccharide from the insoluble complex, during the dissociation of the insoluble complex into the amylase inhibitor and the polysaccharide, or at the insolubilization (gelation) of the dissociated polysaccharide. The filter aid is preferably added during the dissociation of the insoluble complex since the filterability of the insolubilized polysaccharide is further enhanced.

The separation of insolubilized polysaccharide may be achieved by means of such a separation apparatus as a pressure filtration device or a centrifugal separator, with the pressure filtration device being preferable in terms of microfiltration. The type of pressure filtration device is not particularly limited and may be a conventional one, such as YABUTA automatic filtration presser or YAEGAKI automatic filtration presser.

The amylase inhibitor-containing solution recovered in the step (II) may be optionally subjected to sterilization, sanitization, treatment with cation exchange resin (to remove a trypsin inhibitor), etc. Impurities and bacteria may be removed by means of a microfiltration membrane, a porous polymer membrane, a ceramic filter, etc.

The recovered solution containing the amylase inhibitor is then dried by an appropriate method to obtain the amylase inhibitor in the form of solid, such as powder. The amylase inhibitor in dry powder may be obtained by directly drying the concentrated solution of the amylase inhibitor obtained as above or by concentrating the same by vacuum concentration or ultrafiltration and drying the resulting concentrate. The drying may be performed by freeze drying, vacuum drying, spray drying or ball drying.

Otherwise, the concentrate of the amylase inhibitor may be subjected to the steps (B) and (C) of the present process for the preparation of amylase inhibitor, in which the salt is added to the concentrate to insolubilize and separate (salt out) the amylase inhibitor, optionally followed by desalting of the solution, and the solution is dried to obtain the amylase inhibitor in dry powder.

The amylase inhibitor prepared by the present process may be used alone or in combination with conventional carriers or adjuvants in the form of liquid drug, granule or tablet as a hypoglycemic agent and/or an insulin secretion controller. The amylase inhibitor may be also used as food additives, particularly for starch-rich carbohydrate foods, such as bread and cookies; tea; soup; fish or vegetable flakes; and spread, such as butter and jam.

According to the invention, the amylase inhibitor containing in high concentrations 0.19 AI, which shows highly inhibitive activity against the amylase, can be prepared more readily, quickly and with better productivity than conventional methods.

The amylase inhibitor prepared by the present process shows a very high inhibitory activity against the amylase but hardly against trypsin. The amylase inhibitor has a particularly high inhibitory activity against the amylase contained in pancreatic juice so that the insulin secretion can be effectively controlled. Therefore the amylase inhibitor is useful for the prevention and/or treatment of such diseases as hyperglycemia, diabetes, hyperlipidemia, arteriosclerosis and adiposis. Further, the amylase inhibitor obtained by the present process is free from side effects, such as diarrhea and nausea after intake, and is easy to take orally because of its mild taste.

EXAMPLES

The following examples are provided for illustrative purposes only, and are not intended to limit the scope of the present invention.

In the Examples, the content of 0.19 AI was measured in the following manner.

Measurement of 0.19 AI Content

With respect to the amylase inhibitor-containing solution and the insoluble complex of the amylase inhibitor and the polysaccharide, the solid matter resulting from evaporation of water was freeze dried until the water content of not more than 5 wt % was achieved and the resultant powder was used as a sample. The powder was also used as a sample final product of the amylase inhibitor. These samples were individually dissolved in an aqueous solution of 0.1% trifluoroacetic acid, followed by filtration with a 0.45-$\mu$m membrane filter. The filter cake was subjected to high performance liquid chromatography under the conditions shown in Table 1 to measure the peak area for 0.19 AI in the chromatogram. Meanwhile, an authentic sample of 0.19 AI (purity: 100%) was subjected to high performance liquid chromatography under the same conditions to measure the peak area for 0.19 AI in the chromatogram. The 0.19 AI content (wt %) in the sample was calculated according to the following equation (1):

$$0.19 \text{ AI content in the sample (wt \%)} = (Sa/St) \times 100 \quad (1)$$

wherein Sa is the peak area for 0.19 AI in the sample and St is the peak area for 0.19 AI in the authentic sample.

TABLE 1

Conditions in high performance liquid chromatography

| Sample: | solution containing the sample at 1% by mass |
|---|---|
| Sample amount in column: | 10 $\mu$l |
| Column: | |
| packing material: | CAPCELL PAK C18 SG120A |
| (particle size: | 5 $\mu$m, produced by Shiseido Co., Ltd.) |
| size: | 4.6 mm ø × 250 mm |
| temperature: | 50° C. |
| Flow rate: | 0.5 ml/min. |
| Detection: | absorbance at 280 nm |
| Mobile phase (eluting solution): consisting of: | |
| Solution A: | aqueous solution of 0.1% trifluoroacetic acid |
| Solution B: | aqueous solution of 80% acetonitrile and 0.1% trifluoroacetic acid |
| Elution: | high pressure gradient elution with the time/concentration gradient shown below: |

| Time (min) | Solution A (%) | Solution (B) (%) |
|---|---|---|
| 0 | 100 | 0 |
| 5 | 62 | 38 |
| 25 | 62 | 38 |
| 35 | 57 | 43 |
| 40 | 0 | 100 |
| 45 | 0 | 100 |
| 46 | 100 | 0 |

Example 1

(1) Preparation of Aqueous Solution Containing Amylase Inhibitor

To 50,000 kg of wheat flour was added 30 m$^3$ of water and the mixture was kneaded to form a dough. The dough was washed with 400 m$^3$ of water, and gluten 30,000 kg (wet mass) and wheat starch 30,000 kg (dry mass) were recovered. The resulting extract solution 312 m$^3$ was adjusted to the pH 3 by addition of hydrochloric acid, followed by standing for 30 minutes. The pH of the solution was then adjusted to 6 with a sodium hydroxide aqueous solution, as a result of which an insoluble substance was precipitated. The precipitate was removed by a De Laval centrifuge to recover a supernatant liquid 310 m$^3$. According to the measurement by the above method, the supernatant liquid contained 0.19 AI in the proportion of 130 g per 1 m$^3$.

(2) Formation of Insoluble Complex

The supernatant liquid 310 m$^3$ (0.19 AI content: 40.3 kg) recovered in (1) was adjusted to the pH 4.9 with hydrochloric acid and a sodium hydroxide aqueous solution (liquid temperature: 25° C.). Then alginic acid was added thereto in the proportion of 300 ppm, followed by starring for 30 minutes. The pH of the liquid was adjusted to 4.0 by addition of hydrochloric acid, and the liquid was stirred for 30 minutes and then allowed to stand for 2 hours. The precipitate of an insoluble complex of the amylase inhibitor and sodium alginate was recovered by means of a decanter and concentrated by a De Laval centrifuge (BRPX-617 produced by Alfa Laval K.K.). Thus, an insoluble complex (wet matter) 6 m$^3$ was obtained. The measurement for 0.19 AI content by the above method revealed that the insoluble complex thus obtained contained 0.19 AI in an amount of 37.5 kg. That is, 93 wt % of 0.19 AI contained in the supernatant liquid was recovered as the insoluble complex.

(3) Dissociation of Polysaccharide from Insoluble Complex and Recovery of Amylase Inhibitor-Containing Solution (i) To the insoluble complex 6 m$^3$ recovered in (2) was added 2 m$^3$ of purified water of 30° C., and the mixture was stirred for 60 minutes to prepare a suspension 8 m$^3$. Calcium chloride was added to the suspension so as to achieve the calcium concentration 5000 ppm and simultaneously a filter aid (Radiolite #700 produced by Showa Chemical Industry Co., Ltd.) was added in an amount of 60 kg. The mixture solution was stirred for 2 hours at 30° C., and glucanase (Cellulosin TP25 available from HANKYU KYOEI BUSSAN) in an amount of 40 g was added to the solution, followed by 2 hours of stirring at 30° C.

(ii) The suspension obtained in (i) was subjected to pressure filtration by the use of a pressure filter (YABUTA automatic filtration presser 100D-70/48 type produced by Yabuta Kikai K. K.). Prior to the pressure filtration, the filter cloth of the pressure filter was coated with 100 kg of Radiolite #700 and 56.8 kg of Celite 505 (produced by Celite Corporation) under the pressure of 29.4 kPa (0.3 kgf/cm$^2$). The suspension was filtered through the filter cloth with application of pressure within 29.4 to 147.1 kPa (0.3 to 1.5 kgf/cm$^2$). During the pressure filtration, the pressure was maintained within the range of 29.4 to 147.1 kPa (0.3 to 1.5 kgf/cm$^2$) so that the suspension 8 m$^3$ was filtered at a constant flow rate in 1.5 hours. The insolubilized polysaccharide thus collected was washed with 1.5 m$^3$ of purified water. Thus, the filtrate containing the amylase inhibitor was recovered in 8 m$^3$ yield.

(4) Salting Out

To the filtrate 8 m$^3$ containing the amylase inhibitor recovered in (3) was added 1,000 kg of ammonium sulfate, and the mixture was stirred for 2 hours at 8 to 10° C. As a result, salting out was effected to separate an insolubilized substance (salted out product) containing the amylase inhibitor (the pH of the liquid in the salting out was 3.5) The insolubilized substance was recovered by means of a decanter and washed with the equivalent amount of an aqueous solution of 10% ammonium sulfate (w/v). As a result of centrifugal separation, an insolubilized substance was recovered in 250 kg yield (wet mass).

(5) Recovery of Salted Out Product and Desalting

To the insolubilized substance (salted out product) 250 kg in wet condition obtained in (4) was added 2 m$^3$ of purified water, and the mixture was stirred with heating at 50° C. The insolubilized substance was thus dissolved in water to give an aqueous solution, which was then subjected to pressure filtration with a similar small-sized pressure filter likewise in (3). The resulting filtrate was subjected to another filtration to remove bacteria with a ceramic filter (S-86 produced by NIHON ROSUIKI KOGYO CO., LTD) and further to concentration and desalting by means of an ultrafiltration membrane (product of DAICEN MEMBRANE SYSTEMS CO., LTD., polysulfone type having a 30,000 Dalton (molecular weight) cutoff) Thus, a concentrate containing the amylase inhibitor was prepared.

(6) Preparation of Amylase Inhibitor in Dry Powder

The concentrate containing the amylase inhibitor obtained in (5) was kept frozen at −20° C. for 24 hours. The temperature was then stepwise raised from 0° C. to 50° C. at the pressure of 133.3 Pa (1 Torr). As a result of the above freeze drying, dry powder was obtained in 102.9 kg yield.

The 0.19 AI content of the dry powder was 3.86 kg, which means the 0.19 AI recovery of 95.8 wt %.

It took 3 days to complete these treatments (4) to (6) in Example 1.

Example 2

(1) A supernatant liquid containing the amylase inhibitor was prepared in the same manner as in Example 1 (1).

(2) The supernatant liquid obtained in (1) was adjusted to the pH 4, 4.5, 5, 5.5 or to 6 with hydrochloric acid and a sodium hydroxide aqueous solution (liquid temperature: 25° C.) An insoluble complex (wet matter) was recovered from each of the supernatant liquids in the same manner as in Example 1 (2). The 0.19 AI contents in the insoluble complexes (recovery percentages for 0.19 AI from the supernatant liquids) are as shown in Table 2.

TABLE 2

| | pH of the supernatant liquid | | | | |
|---|---|---|---|---|---|
| | 4 | 4.5 | 5 | 5.5 | 6 |
| 0.19 AI recovery (%) | 87 | 92 | 98 | 93 | 81 |

The results in Table 2 show that the amylase inhibitor can be recovered in the form of insoluble complex in high yield by adjusting the amylase inhibitor-containing solution to the pH within 4.5 to 5.5 prior to the addition of polysaccharide in the present step (I) (the step in which the insoluble complex of the amylase inhibitor and the polysaccharide is formed).

Example 3

(1) An insoluble complex of the amylase inhibitor and the polysaccharide was recovered in the same manner as in Example 1 (1) and (2). To the insoluble complex 450 cm$^3$ was added 150 cm$^3$ of purified water of 25° C., and the mixture was stirred for 30 minutes to prepare a suspension 600 cm$^3$. Calcium chloride was added to the suspension so as to achieve the calcium concentration 5000 ppm and simultaneously activated carbon (TAKECOL produced by Takeda Chemical Industries, Ltd.) was added in an amount of 1 g. The mixture solution was stirred for 1 hour at 30° C. and divided in equal six parts, which were incubated for 4 minutes at the liquid temperature of 30, 40, 50, 60, 70 and 80° C. respectively. Thereafter the liquid temperatures were rapidly lowered to 30° C., and the resulting suspensions were subjected to centrifugal separation at 3,000 rpm for 5 minutes to remove the precipitated solid matters, such as the insolubilized polysaccharide dissociated from the insoluble complex. Thus, a supernatant liquid containing the amylase inhibitor was recovered in about 95 cm$^3$ yield in each case.

To determine the color tone of the supernatant liquid, the absorbance at the wavelength 380 nm and 280 nm was measured with respect to each supernatant liquid by a spectrophotometer (U-2010 produced by Hitachi, Ltd.). The results are given in Table 3.

(2) The supernatant liquids containing the amylase inhibitor obtained in (1) were subjected to freeze drying in the same manner as in Example 1 (6) to obtain dry powders containing the amylase inhibitor. The color tone of the amylase inhibitors (dry powders) was observed visually and with reference to a standard color index (New Coloration Cards 199a produced by JAPAN COLOR ENTERPRISE CO., LTD. under the editorship of Japan Color Research Institute). The results are given in Table 3 together with the recovery for 0.19 AI in the dry powder.

TABLE 3

| | Liquid temperature (° C.) in the separation of the polysaccharide from the insoluble complex | | | | | |
|---|---|---|---|---|---|---|
| | 30 | 40 | 50 | 60 | 70 | 80 |
| Absorbance of the supernatant liquid (Brix 1%) at: | | | | | | |
| 380 nm | 1.21 | 1.22 | 1.98 | 0.61 | 0.29 | 0.28 |
| 280 nm | 8.58 | 8.60 | 8.54 | 8.94 | 8.40 | 8.08 |
| Recovery for the amylase inhibitor in dry powder (%) | 100 | 100 | 100 | 100 | 98 | 90 |
| Color tone | | | | | | |
| visually observed | Dark gray | Dark gray | Dark gray | Gray | Ash gray | Ash gray |
| with reference to the standard color index (Gy-brightness value) | 6.0 | 6.0 | 6.0 | 7.5 | 8.5 | 9.0 |

As shown in Table 3, the coloring to brown of the solution containing the amylase inhibitor can be prevented by heating the solution for a short time at 60° C. or above. As a result the liquid will be colorless or a like color instead of the usual brown so that the amylase inhibitor in dry powder obtained therefrom will be excellent in color, taking on a white or like tone.

Example 4

(1) An insoluble complex of the amylase inhibitor and the polysaccharide was recovered in the same manner as in Example 1 (1) and (2).

The polysaccharide separated from the insoluble complex was removed in an insolubilized form by pressure filtration in the same manner as in Example 1 (3) except that the glucanase was used in amounts shown in Table 4. A filtrate containing the amylase inhibitor was recovered in 8 m³ yield in each case. The time required to complete the pressure filtration of the insolubilized polysaccharide in each case is as shown in Table 4.

(2) The filtrates recovered in (1) were subjected to the treatments (4) to (6) of Example 1 to obtain amylase inhibitors in dry powder.

TABLE 4

| | Amount of the glucanase used per 1 m³ of the insoluble complex (g) | | | | | |
|---|---|---|---|---|---|---|
| | 0.1 | 0.5 | 2 | 6 | 12 | 24 |
| Amount of filtrate (m³) | 8 | 8 | 8 | 8 | 8 | 8 |
| Time required for completion of the pressure filtration (hr) | 8 | 4 | 2 | 1.5 | 1.5 | 1.5 |

The results in Table 4 show that the filtration to remove the insolubilized polysaccharide can be smoothly carried out when it is conducted in the presence of glucanase. In particular, the filtration of the insolubilized polysaccharide may be carried out even more smoothly when the glucanase is used in the proportion of 0.5 to 24 g per 1 m³ of the insoluble complex (the state prior to the dissociation therefrom of the polysaccharide).

Example 5

(1) An insoluble complex of the amylase inhibitor and the polysaccharide was recovered in the same manner as in Example 1 (1) and (2).

The polysaccharide separated from the insoluble complex was removed in an insolubilized form by pressure filtration in the same manner as in Example 1 (3) except that a filter aid (Radiolite #700) was used in amounts shown in Table 5. A filtrate containing the amylase inhibitor was recovered in 8 m³ yield in each case. The time required to complete the pressure filtration of the insolubilized polysaccharide in each case is as shown in Table 5.

(2) The filtrates recovered in (1) were subjected to the treatments (4) to (6) of Example 1 to obtain amylase inhibitors in dry powder.

TABLE 5

| | Amount of the filter aid used per 1 m³ of the insoluble complex (g) | | | | | |
|---|---|---|---|---|---|---|
| | 1 | 2.5 | 5 | 10 | 15 | 20 |
| Amount of filtrate (m³) | 8 | 8 | 8 | 8 | 8 | 8 |
| Time required for completion of the pressure filtration (hr) | —[1] | —[1] | 4 | 1.5 | 1.5 | 1.5 |

[1]filtration uncompleted due to the clogging

As apparent from the results shown in Table 5, the filtration to remove the insolubilized polysaccharide can be smoothly carried out with the use of filter aid. In particular, the filtration of the insolubilized polysaccharide may be carried out even more smoothly when the filter aid is used in the proportion of 5 to 20 g per 1 m³ of the insoluble complex.

Reference Example 1

(1) A filtrate containing the amylase inhibitor was recovered in 8 m³ yield in the same manner as in Example 1 (1)–(3).

(2) The filtrate 8 m³ recovered in (1) was neutralized with phosphoric acid and then heated at 80° C. for 30 minutes. The insolubilized substance thus formed was removed by the pressure filter used in Example 1 (3) to recover a supernatant liquid. The supernatant liquid was subjected to concentration and desalting of extra calcium salt by means of an ultrafiltration membrane (product of DAICEN MEMBRANE SYSTEMS CO., LTD., polysulfone type having a 30,000 Dalton (molecular weight) cutoff). Thus, a concentrate was obtained in 4 m³ yield (3) Water was added to the concentrate 4 m³ obtained in (2) so as to achieve the total volume 10 m³. The diluted solution was adjusted to the pH 7.5 with a sodium hydroxide aqueous solution and then passed through a column (1.7 m in length and 1 m in diameter) packed with a cation exchange resin (DIAION HPK-55 produced by Mitsubishi Kasei K.K.) at a flow rate of 1 m³/hr. The fractions eluted through the cation exchange resin without being adsorbed thereon were collected and filtered with the pressure filter used in Example 1 (3). The filtrate was subjected to another filtration to remove bacteria with a ceramic filter (S-86 produced by NIHON ROSUIKI KOGYO CO., LTD) and further to concentration and desalting by means of the ultrafiltration membrane used in (2). The filtrate was freeze dried in the same manner as in Example 1 (6) to obtain an amylase inhibitor in dry powder in 38.4 kg yield. In Reference Example 1, it took 8 days to obtain the amylase inhibitor in dry powder from the filtrate by treatments (2) and (3), the time longer than in Example 1.

Example 6

(1) Preparation of Extract Solution Containing Amylase Inhibitor (Step A)

An extract solution containing the amylase inhibitor was recovered in 310 m³ yield in the same manner as in Example 1 (1). The extract solution contained 0.19 AI in the proportion of 130 g per 1 m³.

(2) Salting Out (Step B)

The extract solution 310 m³ obtained in (1) was concentrated to 77.5 m³ under reduced pressure (the protein concentration in the concentrate was 10.8 mg/cm³), and adjusted to the pH 3.5 with hydrochloric acid. To the resulting concentrate were added sodium chloride 11,600 kg (the amount achieving 15 wt % sodium chloride concentration in the concentrate) and calcium chloride 860 kg (the amount achieving 4,000 ppm calcium ion concentration in the liquid), and they were stirred at 4° C. for 2 hours to effect the salting out (the pH of the liquid in the salting out was 3.5). As a result, an insolubilized substance (salted out product) containing the amylase inhibitor occurred. The insolubilized substance was recovered by means of a filter press, washed with the equivalent amount of an aqueous solution of 15% sodium chloride (w/v), and subjected to filtration with a filter press. Thus, an insolubilized substance (salted out product) was recovered in 320 kg yield (wet mass). The protein concentration in the liquid was measured with DC Protein Assay Kit (produced by Bio-Rad Laboratories, Inc.).

(3) Desalting and Recovery of Amylase Inhibitor (Step C)

Purified water 4 m³ was added to the insolubilized substance (salted out product) 320 kg obtained in (2), and the both were stirred with heating at 40° C., thereby dissolving the insolubilized substance in water. The resulting aqueous solution was subjected to filtration with a filter (YABUTA filtration presser 66-D-22 type) and to another filtration to remove bacteria with a ceramic filter (S-86 produced by NIHON ROSUIKI KOGYO CO., LTD). The filtrate was further subjected to concentration and desalting by means of an ultrafiltration membrane (product of DAICEN MEMBRANE SYSTEMS CO., LTD., polystyrene type having a 30,000 Dalton (molecular weight) cutoff). Thus, a concentrate containing the amylase inhibitor was prepared. The concentrate was kept frozen at −20° C. for 24 hours. The temperature was then stepwise raised from 0° C. to 50° C. at the pressure of 133.3 Pa (1 Torr) As a result of the above freeze drying, dry powder was obtained in 192 kg yield. The 0.19 AI content of the dry powder was 40.3 kg, which means the 0.19 AI recovery of 100%.

Example 7

Amylase inhibitors in dry powder were prepared in the same manner as in Example 6 except that the concentrate (concentrated supernatant liquid) was adjusted to the pH 2.5, 3.0, 3.5, 4.0 or to 4.5 prior to the addition of sodium chloride. The 0.19 AI contents in the dry powders were measured to determine the 0.19 AI recovery. The results are given in Table 6.

TABLE 6

| | pH of the concentrate | | | | |
|---|---|---|---|---|---|
| | 2.5 | 3.0 | 3.5 | 4.0 | 4.5 |
| 0.19 AI recovery (%) | 72 | 92 | 100 | 91 | 85 |

The results in Table 6 show that the amylase inhibitor (0.19 AI) can be recovered in high yield by adjusting the amylase inhibitor-containing solution to the pH 3 to 4, particularly to the pH 3.5 prior to the addition of sodium chloride.

Example 8

(1) Amylase inhibitors in dry powder were prepared in the same manner as in Example 6 except that the extract solution containing the amylase inhibitor, adjusted to the pH 3.5 with hydrochloric acid, was concentrated to the degrees shown in Table 7 and that the salting out was effected with the concentrations of sodium chloride and of calcium ion in the solution changed as shown in Table 7. The protein concentrations in the supernatant liquids or concentrates thereof prior to the salting out are set forth in Table 7. The protein concentrations in the liquid were determined in the same manner as in Example 6.

(2) The 0.19 AI contents in the dry powders were measured to determine the 0.19 AI recovery. The results are given in Table 7.

TABLE 7

| Expr. No. | AI-containing solution | Protein concentration[1] (wt %) | NaCl concentration (wt %) | Ca ion concentration (ppm) | 0.19 AI recovery (%) |
|---|---|---|---|---|---|
| 1 | unconcentrated | 2.7 | 15 | — | 6.4 |
| 2 | unconcentrated | 2.7 | 25 | — | 67.9 |
| 3 | unconcentrated | 2.7 | 15 | 4000 | 17.2 |
| 4 | unconcentrated | 2.7 | 25 | 4000 | 87.1 |
| 5 | unconcentrated | 2.7 | 15 | 6000 | 19.8 |
| 6 | unconcentrated | 2.7 | 25 | 6000 | 90.3 |
| 7 | concentrated[2] | 5.4 | 15 | — | 70.5 |
| 8 | concentrated[2] | 5.4 | 25 | — | 90.8 |
| 9 | concentrated[2] | 5.4 | 15 | 4000 | 82.3 |
| 10 | concentrated[2] | 5.4 | 25 | 4000 | 97.7 |
| 11 | concentrated[2] | 5.4 | 15 | 6000 | 95.1 |
| 12 | concentrated[2] | 5.4 | 25 | 6000 | 99.4 |
| 13 | concentrated[3] | 10.8 | 15 | — | 98.0 |
| 14 | concentrated[3] | 10.8 | 25 | — | 100 |
| 15 | concentrated[3] | 10.8 | 15 | 4000 | 100 |
| 16 | concentrated[3] | 10.8 | 25 | 4000 | 100 |
| 17 | concentrated[3] | 10.8 | 15 | 6000 | 100 |
| 18 | concentrated[3] | 10.8 | 25 | 6000 | 100 |

[1]unit: mg/cm³
[2]½-volume concentrate of the solution (supernatant liquid containing the amylase inhibitor) of Experiment No. 1
[3]¼-volume concentrate of the solution (supernatant liquid containing the amylase inhibitor) of Experiment No. 1

Example 9

(1) Preparation of Aqueous Solution Containing Amylase Inhibitor (Step A)

To 50,000 kg of wheat flour was added 30 m³ of water and the mixture was kneaded to form a dough. The dough was washed with 400 m³ of water, and gluten 30,000 kg (wet mass) and wheat starch 30,000 kg (dry mass) were recovered. The resulting extract solution 312 m³ was measured for the protein concentration in the same manner as in Example 1, which was found to be 4.2 mg/cm$^3$. The extract solution contained 0.19 AI in the proportion of 129.2 g per 1 m$^3$.

(2) Salting Out (Step B) and Desalting and Recovery of Amylase Inhibitor (Step C)

An amylase inhibitor in dry powder was prepared from the extract solution 312 m$^3$ obtained in (1) in the same manner as in Example 6 except that the extract solution containing the amylase inhibitor, adjusted to the pH 3.5 with hydrochloric acid, was concentrated to the degrees shown in Table 8 and that the salting out was effected with the concentrations of sodium chloride and of calcium ion in the solution changed as shown in Table 8. The protein concentrations in the extract solutions or concentrates thereof prior to the salting out were measured in the same manner as in Example 6. The results are set forth in Table 8. (3)

The 0.19 AI contents in the dry powders were measured to determine the 0.19 AI recovery. The results are given in Table 8.

TABLE 8

| Expr. No. | AI-containing solution | Protein concentration[1] | NaCl concentration (wt %) | Ca ion concentration (ppm) | 0.19 AI recovery (%) |
|---|---|---|---|---|---|
| 1 | unconcentrated | 4.2 | 15 | — | 2.7 |
| 2 | unconcentrated | 4.2 | 25 | — | 55.0 |
| 3 | unconcentrated | 4.2 | 15 | 4000 | 14.8 |
| 4 | unconcentrated | 4.2 | 25 | 4000 | 80.2 |
| 5 | unconcentrated | 4.2 | 15 | 6000 | 17.5 |
| 6 | unconcentrated | 4.2 | 25 | 6000 | 88.2 |
| 7 | concentrated[2] | 8.4 | 15 | — | 66.1 |
| 8 | concentrated[2] | 8.4 | 25 | — | 87.4 |
| 9 | concentrated[2] | 8.4 | 15 | 4000 | 78.3 |
| 10 | concentrated[2] | 8.4 | 25 | 4000 | 95.5 |
| 11 | concentrated[2] | 8.4 | 15 | 6000 | 86.6 |
| 12 | concentrated[2] | 8.4 | 25 | 6000 | 97.2 |
| 13 | concentrated[3] | 16.8 | 15 | — | 97.9 |
| 14 | concentrated[3] | 16.8 | 25 | — | 100 |
| 15 | concentrated[3] | 16.8 | 15 | 4000 | 100 |
| 16 | concentrated[3] | 16.8 | 25 | 4000 | 100 |
| 17 | concentrated[3] | 16.8 | 15 | 6000 | 100 |
| 18 | concentrated[3] | 16.8 | 25 | 6000 | 100 |

[1] unit: mg/cm$^3$
[2] ½-volume concentrate of the solution (supernatant liquid containing the amylase inhibitor) of Experiment No. 1
[3] ¼-volume concentrate of the solution (supernatant liquid containing the amylase inhibitor) of Experiment No. 1

Example 10

An amylase inhibitor in dry powder was obtained in 202 kg yield in the same manner as in Example 6 except that 12,000 kg of ammonium sulfate was used in the salting out in place of 11,600 kg of sodium chloride. The 0.19 AI content in the amylase inhibitor in dry powder was measured by the above method, and the 0.19 AI recovery was found to be 100%.

Example 11

(1) A supernatant liquid containing the amylase inhibitor was obtained in 310 m$^3$ yield in the same manner as in Example 6 (1) The supernatant liquid was concentrated to 77.5 m$^3$ by distilling off the water content under reduced pressure (the protein concentration in the concentrate was 10.8 mg/cm$^3$), and adjusted to the pH 3.5 with hydrochloric acid. The resulting concentrate was brown.

(2) To the concentrate 77.5 m$^3$ obtained in (1) were added sodium chloride 11,600 kg. (the amount achieving 15 wt % sodium chloride concentration in the concentrate) and calcium chloride 860 kg (the amount achieving 4,000 ppm calcium ion concentration in the liquid), and further ascorbic acid in amounts shown in Table 9. They were stirred at 4° C. for 2 hours to effect the salting out. As a result, an insolubilized substance (salted out product) containing the amylase inhibitor occurred in each case. The insolubilized substances were each recovered by a decanter, washed with the equivalent amount of an aqueous solution of 10% ammonium sulfate (w/v), and recovered a salted out product in wet condition by means of a decanter.

(3) The salted out products obtained in (2) were subjected to concentration, desalting and drying in the same manner as in Example 6 (3) to give dry powders. The 0.19 AI contents in the dry powders were measured to determine the 0.19 AI recovery, which was in each case approximately 100% irrespective of the amount of ascorbic acid. The dry powders obtained as above were visually observed for color tone, and the brightness thereof was evaluated in the same manner as in Example 3 (2). The results are given in Table 9.

TABLE 9

| | Amount of ascorbic acid used per 1 m$^3$ of the concentrate (g) | | | | | |
|---|---|---|---|---|---|---|
| | 0 | 10 | 50 | 100 | 300 | 1000 |
| Color tone | | | | | | |
| visually observed | Dark gray | Gray | Ash gray | Ash gray | Ash gray | Ash gray |
| with reference to the standard color index (Gy-brightness value) | 6.0 | 7.5 | 8.5 | 9.0 | 9.0 | 9.0 |

The results in Table 9 show that the coloring of the amylase inhibitor-containing solution can be prevented by addition of ascorbic acid. As a result the amylase inhibitor obtained therefrom in dry powder will be excellent in color, taking on a white or like tone.

Example 12

Amylase inhibitors in dry powder were obtained in the same manner as in Example 9 (1)-(3) except that cysteine was used in place of ascorbic acid. The 0.19 AI contents in the dry powders were measured to determine the 0.19 AI recovery, which was in each case approximately 100% irrespective of the amount of cysteine. The dry powders obtained as above were visually observed for color tone, and the brightness thereof was evaluated in the same manner as in Example 11 The results are given in Table 10.

TABLE 10

| | Amount of cysteine used per 1 m$^3$ of the concentrate (g) | | | | | |
|---|---|---|---|---|---|---|
| | 0 | 15 | 45 | 145 | 450 | 1450 |
| Color tone | | | | | | |
| visually observed | Dark gray | Dark gray | Gray | Gray | Ash gray | Ash gray |
| with reference to the standard color index (Gy-brightness value) | 6.0 | 6.0 | 7.0 | 7.5 | 8.5 | 9.0 |

The results in Table 10 show that the coloring of the solution containing the amylase inhibitor can be prevented by addition of cysteine. As a result the amylase inhibitor obtained therefrom in dry powder will be excellent in color, taking on a white or like tone.

Example 13

(1) A supernatant liquid containing the amylase inhibitor was obtained in 310 m³ yield in the same manner as in Example 6 (1) The supernatant liquid contained 0.19 AI in the proportion of 130 g per 1 m³.

(2) The supernatant liquid 310 m³ obtained in (1) (the 0.19 AI content: 40.3 kg) was treated in the same manner as in Example 1 (2) and (3) except that alginic acid was added to the supernatant liquid in the proportion of 300 ppm before the liquid was adjusted to the pH 4.9 (liquid temperature: 25° C.) with hydrochloric acid and the sodium hydroxide aqueous solution. Thus, a filtrate containing the amylase inhibitor was recovered in 8 m³ yield.

(3) To the filtrate 8 m³ obtained in (2) was added 500 kg of sodium chloride, and the mixture was stirred for 2 hours at 8 to 10° C. As a result, salting out was effected to separate an insolubilized substance (salted out product) containing the amylase inhibitor (the liquid pH in the salting out was 3.5). The insolubilized substance was recovered by means of a decanter, washed with the equivalent amount of an aqueous solution of 10% sodium chloride (w/v), and recovered an insolubilized substance in 250 kg yield (wet mass) by means of a decanter.

(4) To the insolubilized substance 250 kg obtained in (3) was added 2 m³ of purified water, and the mixture was stirred with heating at 50° C. The insolubilized substance was thus dissolved in water to give an aqueous solution, which was then subjected to pressure filtration with a small-sized pressure filter (YABUTA automatic filtration presser produced by Yabuta Kikai K.K.) under the same conditions of Example 1 (5). The filtrate was subjected to another filtration to remove bacteria with a ceramic filter (S-86 produced by NIHON ROSUIKI KOGYO CO., LTD) and further to concentration and desalting by means of an ultrafiltration membrane (product of DAICEN MEMBRANE SYSTEMS CO., LTD., polysulfone type having a 30,000 Dalton (molecular weight) cutoff). Thus, a concentrate containing the amylase inhibitor was prepared.

(5) The concentrate containing the amylase inhibitor obtained in (4) was kept frozen at −20° C. for 24 hours. The temperature was then stepwise raised from 0° C. to 50° C. at the pressure of 133.3 Pa (1 Torr). As a result of the above freeze drying, dry powder was obtained in 109.7 kg yield.

The 0.19 AI content of the dry powder was 39.5 kg, meaning the 0.19 AI recovery of 98 wt %.

It took 3 days to complete these treatments (3) to (5) in this Example.

(6) When the above filtrate containing the amylase inhibitor was separately subjected to the salting out likewise in (3) with alteration of the pH to either 3 or 4, the recovery for the final product 0.19 AI was 87% in the case of the pH 3 and 89% in the case of the pH 4.

The above results revealed that the salting out may be effected favorably to achieve extremely high recovery for 0.19 AI when the filtrate containing the amylase inhibitor has been adjusted to the pH 3.5.

Example 14

Amylase inhibitors (in dry powder) were prepared in the same manner as in Example 13 except that the salting out was effected by addition of sodium chloride in amounts shown in Table 11. The 0.19 AI recovery in each case is set forth in Table 11.

TABLE 11

| | Amount of sodium chloride used per 1 m³ of the IA-containing filtrate (kg) | | | | |
|---|---|---|---|---|---|
| | 10 | 30 | 50 | 100 | 200 |
| 0.19 AI recovery (%) | 37 | 80 | 98 | 100 | 100 |

Example 15

An amylase inhibitor was prepared in the same manner as in Example 13 except that the salting out was effected with 1,000 kg of ammonium sulfate in place of 500 kg of sodium chloride. The 0.19 AI recovery was 95.8%.

Example 16

(1) A filtrate containing the amylase inhibitor was recovered in 8 m³ yield in the same manner as in Example 13 (1) and (2). The filtrate was brown. According to the measurement with a spectrophotometer (U-2010 produced by Hitachi, Ltd.), the filtrate had the absorbance of 1.28 and 14.98 at the wavelength 380 nm and 280 nm, respectively.

(2) To the filtrate 8 m³ obtained in (1) were added 1,000 kg of ammonium sulfate and ascorbic acid in amounts shown in Table 12. They were stirred for 2 hours at 8 to 10° C. As a result, salting out was effected to separate an insolubilized substance (salted out product) containing the amylase inhibitor in each case. The insolubilized substances were each recovered by a decanter, washed with the equivalent amount of an aqueous solution of 10% ammonium sulfate (w/v), then an insolubilized substance was recovered by means of a decanter in 250 kg yield in each case.

(3) Purified water 2 m³ was added to each of the insolubilized substances (salted out products) 250 kg obtained in (2), and the insolubilized substance was dissolved therein to give an aqueous solution in each case. The solutions thus prepared were then subjected to concentration and desalting in the same manner as in Example 13 (4) to prepare concentrates containing the amylase inhibitor. The resulting concentrates were visually observed for color tone, and the absorbance at the wavelength 380 nm and 280 nm was determined with the spectrophotometer used in (1) The results are given in Table 12.

(4) The concentrates containing the amylase inhibitor obtained in (3) were subjected to freeze drying in the same manner as in Example 13 (5) to obtain an amylase inhibitor in dry powder in each case. The color tone of the dry powders was visually observed, and the brightness thereof was evaluated in the same manner as in Example 11, the results being shown in Table 12. The 0.19 AI recovery was in the range of 94 to 96% in each case.

TABLE 12

| | Amount of ascorbic acid used per 1 m³ of the concentrate (g) | | | | | |
|---|---|---|---|---|---|---|
| | 0 | 10 | 50 | 100 | 300 | 1000 |
| Visually-observed color tone of the concentrate | Dark brown | Ocher | Yellow | Yellow | Light yellow | Light yellow |

TABLE 12-continued

| | Amount of ascorbic acid used per 1 m³ of the concentrate (g) | | | | | |
|---|---|---|---|---|---|---|
| | 0 | 10 | 50 | 100 | 300 | 1000 |
| Absorbance at: | | | | | | |
| 380 nm | 42.2 | 13.1 | 5.3 | 4.0 | 3.4 | 1.9 |
| 280 nm | 28.1 | 22.5 | 19.6 | 18.5 | 17.7 | 17.2 |
| Color tone of the amylase inhibitor visually observed | Dark gray | Gray | Ash gray | Ash gray | Ash gray | Ash gray |
| with reference to the standard color index (Gy-brightness value) | 6.0 | 7.5 | 8.5 | 9.0 | 9.0 | 9.0 |

The results in Table 12 show that addition of ascorbic acid enables inhibition of coloring of the solution containing the amylase inhibitor. The effect of coloring inhibition is excellently attained particularly when ascorbic acid is added to the solution in the proportion of 1 to 1,000 g per 1 m³

Example 17

(1) Concentrates containing the amylase inhibitor were prepared in the same manner as in Example 16 (1) and (2) except that cysteine was used in place of ascorbic acid. The concentrates were visually observed for color tone, and the absorbance at the wavelength 380 nm and 280 nm was determined in the same manner as in Example 16. The results are given in Table 13.

(2) The concentrates obtained in (1) were subjected to freeze drying in the same manner as in Example 13 (5.) to obtain amylase inhibitors in dry powder. The color tone of the dry powders was visually observed, and the brightness thereof was evaluated in the same manner as in Example 11, the results being shown in Table 13.

TABLE 13

| | Amount of cysteine used per 1 m³ of the concentrate (g) | | | | | |
|---|---|---|---|---|---|---|
| | 0 | 15 | 45 | 145 | 450 | 1450 |
| Visually-observed color tone of the concentrate | Dark brown | Dark brown | Brown | Ocher | Yellow | Light yellow |
| Absorbance at: | | | | | | |
| 380 nm | 42.2 | 32.8 | 18.2 | 11.5 | 4.6 | 2.1 |
| 280 nm | 28.1 | 24.3 | 23.6 | 22.2 | 18.8 | 17.1 |
| Color tone of the amylase inhibitor visually observed | Dark gray | Dark gray | Gray | Gray | Ash gray | Ash gray |
| with reference to the standard color index (Gy-brightness value) | 6.0 | 6.0 | 7.0 | 7.5 | 8.5 | 9.0 |

The results in Table 13 show that addition of cysteine enables inhibition of coloring of the solution containing the amylase inhibitor. The effect of coloring inhibition is excellently attained particularly when cysteine is added to the solution in the proportion of 15 to 10,000 g per 1 m³.

What is claimed is:

1. A process for a preparation of amylase inhibitor, comprising:
   (A) a step of obtaining an extract solution containing the amylase inhibitor by:
   (A1) extracting wheat flour or wheat gluten with water, an acidic aqueous solution, an alkali aqueous solution or an aqueous alcohol,
   (A2) extracting wheat flour or wheat gluten with water, an acidic aqueous solution, an alkali aqueous solution or an aqueous alcohol; acid-treating and/or heat-treating the resulting solution to denature the contaminants; and removing the denatured contaminants from the solution, or
   (A3) adjusting the pH of an extract solution containing the amytase inhibitor obtained in (A1) or (A2) within the range of 4.5 to 5.5, adding a polysaccharide to the solution to form an association product of the amylase inhibitor and the polysaccharide in the solution and then adjusting the pH within the range of 3.0 to 4.0 to form an insoluble complex of the amylase inhibitor and the polysaccharide;
   recovering the insoluble complex;
   and dissociating the polysaccharide from the insoluble complex in a liquid to remove the polysaccharide in an insolubilized form from the liquid;
   (B) a step of insolubilizing the amylase inhibitor by salting out by addition of a salt or salts to the amylase inhibitor-containing solution obtained in the step (A) and recovering the insolubilized substance resulting from the salting out; and
   (C) a step of directly drying the insolubilized substance recovered in the step (B) or dissolving the insolubilized substance in water to prepare an aqueous solution, and desalting and drying the aqueous solution to recover the amylase inhibitor.

2. The process according to claim 1, wherein the salt in the step (B) is sodium chloride.

3. The process according to claim 1, wherein the salting out in the step (B) is carried out in the presence of calcium ions in the extract solution.

4. The process according to claim 1, wherein the salting out in the step (B) is carried out in the extract solution at a pH within the range of 3 to 4.

5. The process according to claim 1, wherein the extract solution containing the amylase inhibitor obtained in step (B) has a protein concentration of 1 to 100 mg/cm³.

6. The process according to claim 1, further comprising adding ascorbic acid and/or cysteine to at least one of the amylase-containing solution of step (B) and the aqueous solution of step (C).

7. The process according to claim 1, wherein the polysaccharide is dissociated from the insoluble complex of the amylase inhibitor and the polysaccharide in the presence of glucanase, and the dissociated polysaccharide is removed in an insolubilized form by filtration.

8. The process according to claim 7, wherein the filtration is carried out with addition of a filter aid.

9. The process according to claim 1, wherein the solution containing the amylase inhibitor is heated at 50° C. or above during or after the dissociation of the polysaccharide.

10. A process for concentration an extract solution containing an amylase inhibitor, comprising the steps of:
   (I) adjusting the pH of an extract solution containing an amylase inhibitor produced in step (A1) or step (A2) of claim 1 within the range of 4.5 to 5.5, adding a polysaccharide to the solution to form an association product of the amylase inhibitor and the polysaccharide in the solution and then adjusting the pH within the range of 3.0 to 4.0 to form an insoluble complex of the amylase inhibitor and the polysaccharide; and (II) separating the insoluble complex from the solution, dissociating the polysaccharide from the insoluble complex, and removing the polysaccharide in an insolubilized form from the solution to recover the amylase inhibitor in the form of solution.

11. The process of claim 10, wherein the polysaccharide is dissociated from the insoluble complex of the amylase inhibitor and the polysaccharide in the presence of glucanase, and the dissociated polysaccharide is removed in an insolubilized form by filtration.

12. The process of claim 11, wherein the filtration is carried out with addition of a filter aid.

13. The process of claim 10, wherein the solution containing the amylase inhibitor is heated at 50° C. or above during or after the dissociation of the polysaccharide.

* * * * *

UNITED STATES PATENT AND TRADEMARK OFFICE
CERTIFICATE OF CORRECTION

PATENT NO.   : 6,858,234 B2
DATED        : February 22, 2005
INVENTOR(S)  : Murayama et al.

It is certified that error appears in the above-identified patent and that said Letters Patent is hereby corrected as shown below:

<u>Column 24,</u>
Line 17, "amytase inhibitor" should read -- amylase inhibitor --.
Line 64, "concentration an extract" should read -- concentrating an extract --.

Signed and Sealed this

Twentieth Day of September, 2005

JON W. DUDAS
*Director of the United States Patent and Trademark Office*